United States Patent [19]

Franke et al.

[11] Patent Number: 4,791,123

[45] Date of Patent: Dec. 13, 1988

[54] INSECTICIDAL TRIFFLUORMETHYL ALKANE DERIVATIVES

[75] Inventors: Helga Franke; Heinrich Franke; Hans-Rudolf Krüger; Hartmut Joppien; Dietrich Baumert; David Giles, all of Berlin, Fed. Rep. of Germany

[73] Assignee: Schering Akt., Fed. Rep. of Germany

[21] Appl. No.: 6,565

[22] Filed: Jan. 22, 1987

[30] Foreign Application Priority Data

Jan. 22, 1986 [DE] Fed. Rep. of Germany ....... 3602169

[51] Int. Cl.$^4$ .............................................. A01N 43/40
[52] U.S. Cl. ...................... 514/345; 514/337; 514/338; 514/346; 514/347; 514/348; 514/349; 514/350; 514/351; 514/352; 514/353; 514/354; 514/355; 514/357; 514/379; 514/443; 514/450; 514/452; 514/469; 514/470; 514/506; 514/510; 514/520; 514/524; 514/525; 514/646; 514/648; 514/654; 514/655; 514/657; 514/658; 514/676; 514/677; 514/679; 514/680; 514/681; 514/682; 514/685; 514/686; 514/712; 514/713; 514/716; 514/717; 514/720; 514/721; 514/741; 514/749; 548/241; 570/128; 570/129; 546/269; 546/270; 546/274; 546/292; 546/294; 546/295; 546/296; 546/297; 546/298; 546/299; 546/300; 546/301; 546/302; 546/303; 546/304; 546/306; 546/307; 546/308; 546/309; 546/310; 546/312; 546/314; 546/315; 546/328; 514/329; 514/330; 514/332; 514/333; 514/334; 514/338; 514/339; 514/343; 514/346; 549/49; 549/51; 549/52; 549/53; 549/55; 549/56; 549/57; 549/58; 549/350; 549/363; 549/466; 549/467; 549/469; 549/474; 558/58; 558/388; 558/389; 558/404; 558/405; 558/408; 558/410; 558/415; 558/418; 558/472; 558/423; 558/424; 558/425; 564/367; 564/370; 564/371; 564/374; 564/381; 564/382; 564/384; 564/431; 564/433; 568/43; 568/44; 568/49; 568/52; 568/56; 568/327; 568/328; 568/583; 568/585; 568/586; 568/634; 568/637; 568/639; 568/642; 568/643; 568/645; 568/660; 568/661; 568/928; 568/929; 474/DIG. 8

[58] Field of Search ............... 568/639, 637, 43, 44, 568/49, 52, 56, 327, 328, 585, 586, 583, 634, 642, 643, 645, 660, 661; 514/717, 721, 345, 337, 338, 346, 347, 348, 349, 350, 351, 352, 353, 354, 355, 357, 379, 443, 450, 452, 469, 470, 506, 510, 520, 524, 525, 646, 648, 654; 546/302, 303, 269, 270, 274, 292, 294, 295, 296, 297, 298, 299, 300, 301, 304, 306, 307, 308, 309, 310, 312, 314, 315, 328, 329, 330, 332, 333, 334, 338, 339, 343, 346; 570/129, 128; 548/241; 549/49, 51, 52, 53, 55, 56, 57, 58, 350, 363, 466, 467, 469, 471; 558/58, 388, 389, 404, 405, 408, 410, 415, 418, 422, 423, 424, 425; 564/367, 370, 371, 374, 381, 382, 384, 431, 433; 574/655, 657, 658, 676, 677, 679, 680, 681, 682, 685, 686, 687, 712, 713, 716, 720, 741, 749; 424/DIG. 8

[56] References Cited

U.S. PATENT DOCUMENTS

| | | | |
|---|---|---|---|
| 3,998,855 | 12/1976 | Karrer | 424/DIG. 8 |
| 4,266,074 | 5/1981 | Fujimoto et al. | 560/105 |
| 4,316,994 | 2/1982 | Fuchs et al. | 568/639 |
| 4,326,087 | 4/1982 | Fuchs et al. | 568/639 |
| 4,397,864 | 8/1983 | Nakatani et al. | 568/42 |
| 4,570,005 | 2/1986 | Nakatani et al. | 568/42 |
| 4,661,501 | 4/1987 | Nakatani et al. | 568/631 |
| 4,664,698 | 5/1987 | Tsushima et al. | 546/302 |

FOREIGN PATENT DOCUMENTS

| | | | |
|---|---|---|---|
| 0008734 | 3/1980 | European Pat. Off. | 568/639 |
| 0175377 | 3/1986 | European Pat. Off. | 546/302 |
| 154931 | 12/1980 | Japan | 568/639 |
| 29733 | 2/1983 | Japan | 568/639 |
| 193940 | 10/1985 | Japan | 568/639 |

Primary Examiner—Michael L. Shippen
Assistant Examiner—Bruce D. Gray
Attorney, Agent, or Firm—Ostrolenk, Faber, Gerb & Soffen

[57] ABSTRACT

There are provided new alkane and alkoxyalkane derivatives of the general formula I

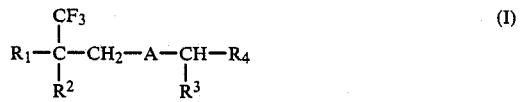

(I)

in which $R_1$, $R_2$, $R_3$, $R_4$ and A have the meanings given in the description, processes for their preparation and insecticidal and acaricidal compositions containing these compounds.

12 Claims, No Drawings

INSECTICIDAL TRIFFLUORMETHYL ALKANE DERIVATIVES

The invention relates to new alkane and alkoxyalkane derivatives, processes for their preparation and insecticidal and acaricidal compositions containing these compounds.

It is already known that certain alkane and alkoxyalkane derivatives possess insecticidal and acaricidal properties (DE-OS No. 31 17 510 and DE-OS No. 33 17 908).

The object of the present invention is the preparation of new compounds that combat insects and spider mites better than compounds known for this purpose.

The alkane and alkoxyalkane derivatives of the invention are of the general formula I

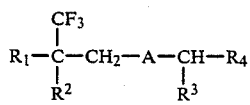

in which
$R_1$ is aromatic or aromatic substituted by $C_{1-4}$ alkyl, halo-$C_{1-4}$ alkyl, phenyl-$C_{1-4}$ alkyl, $C_{2-4}$ alkenyl, halo-$C_{2-4}$ alkenyl, phenyl-$C_{2-4}$ alkenyl, $C_{2-4}$ alkynyl, halo-$C_{2-4}$ alkynyl, phenyl-$C_{2-4}$ alkynyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{2-4}$ alkynyloxy, alkylsulphonyloxy, haloalkylsulphonyloxy, arylsulphonyloxy, halo, cyano, nitro, aryloxy, haloaryloxy, $C_{1-4}$alkyl-aryloxy, or nitroaryloxy,
$R_2$ is hydrogen or $C_{1-4}$ alkyl,
$R_3$ is hydrogen, cyano or ethynyl,
$R_4$ is phenyl or pyridyl or these groups substituted by one or more of $C_{1-6}$ alkyl, halo-$C_{1-6}$ alkyl, phenyl-$C_{1-6}$ alkyl, $C_{2-6}$ alkyl interrupted by an O-, N- or S-atom, $C_{2-4}$ alkenyl, halo-$C_{2-4}$ alkenyl, phenyl-$C_{2-4}$ alkenyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{2-4}$ alkynyloxy, aryloxy, haloaryloxy, $C_{1-4}$ alkylaryloxy, arylamino, haloarylamino, $C_{1-4}$ alkylarylamino, aryl-N-$C_{1-4}$ alkylamino, aryl-N-$C_{1-4}$ acylamino, aroyl, haloaroyl, $C_{1-4}$ alkylaroyl, aryl, haloaryl, $C_{1-4}$ alkylaryl or halo, and
A is $C_2$ or O.

It has been found that these compounds have a better insecticidal and acaricidal activity than structurally similar compounds.

The compounds of the invention are surprisingly highly active against a number of important plant pests, such as for example *Plutella xylostella, Epilachna verivestis* and *Spodoptera littoralis*. For this activity, highly active insecticides are known that can be used for combating these plant pests. The compounds of the invention also have activity against a number of economically important animal ectoparasites and public health pests.

The aromatic group designated as $R_1$ in general formula I includes aryl and heteroaryl such as phenyl, 1-naphthyl, 2-naphthyl, benzofuran-5-yl, benzothiophen-5-yl, benzofuran-6-yl, benzothiophen-6-yl, benzoxazol-5-yl, benzoxazol-6-yl, indan-5-yl, indan-6-yl, 1,4-benzodioxan-6-yl, 1,3-benzodioxan-6-yl, 1,3-benzodioxan-7-yl, 1,3-benzodioxol-5-yl and 5,6,7,8-tetrahydronaphthyl.

Compounds of the invention showing particularly good insecticidal and acaricidal activity are those in which in general formula I
$R_1$ is chlorophenyl, bromophenyl, fluorophenyl, methylphenyl, methoxyphenyl, ethoxyphenyl, difluoromethoxyphenyl, fluorethoxyphenyl, or trifluoroethoxyphenyl,
$R_2$ is hydrogen or methyl,
$R_3$ is hydrogen,
$R_4$ is phenoxyphenyl, fluorophenoxyphenyl or phenoxypyridyl and
A is $CH_2$ or O.

The compounds of the invention exist as optional isomers. The invention includes all isomers as well as mixtures of them.

The compounds of the invention, where $A=CH_2$, can be prepared for example
(a) reacting a compound of general formula II

or of general formula III

first with a base and then with a compound of general formula IV

to give a compound of general formula V

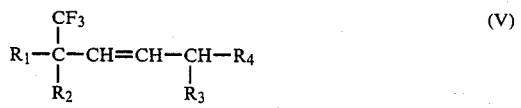

and then reducing this to the desired product, or
(b) reacting a compound of general formula VI

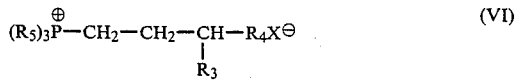

first with a base and then with a compound of general formula VII

to give a compound of general formula VIII

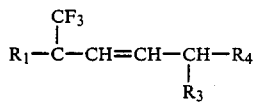 (VIII)

and then reducing this to the desired product, or
(c) condensing a compound of general formula IX

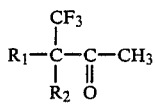 (IX)

with an aldehyde of general formula X

R₄CHO (X)

to given an α,β-unsaturated compound of general formula XI

 (XI)

and then reducing this to the desired product or
(d) condensing a compound of general formula XII $$R_4-C-CH_3$$
$$\parallel$$
$$O$$ (XII)

with an aldehyde of general formula IV

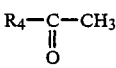 (IV)

to give an α,β-unsaturated compound of general formula XIII

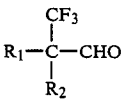 (XIII)

and then reducing this to the desired product, in which $R_1$, $R_2$, $R_3$ and $R_4$ have the meanings given above and $R_5$ is alkyl or phenyl, $R_6$ is is alkyl and X is halogen.

The compounds of the invention, where A=O, can be prepared for example
(a) reacting a compound of general formula XIV

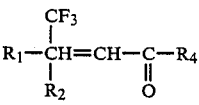 (XIV)

with a compound of general formula XV

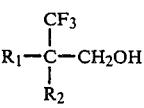 (XV)

in the presence of a base and using a solvent, or (b) reacting a compound of general formula XVI

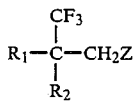 (XVI)

with a compound of general formula XVII

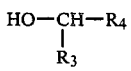 (XVII)

in the presence of a base and using a solvent, in which $R_1$, $R_2$, $R_3$ and $R_4$ have the meanings given above and Z is halogen, methanesulphonate or toluenesulphonate.

The reaction with the phosphonium salts or the phosphonates of general formula II, III and VI can be carried out, for example in the presence of an inert solvent, such as that generally used in Wittig reactions. Suitable solvents include alaphatic or aromatic hydrocarbons, such as for example hexane, benzene or toluene, and ethers such as for example diethyl ether and tetrahydrofuran. Other suitable solvents are amides, such as dimethylformamide or hexamethylphosphoric acid triamide. In some cases, alcohols or dimethyl sulphoxide can be used.

Suitable bases for the Wittig reaction include metal alcoholates, such as for example sodium ethanolate, metal hydrides, such as for example sodium hydride, metal amides, such as for example sodium amide and organometalic compounds, such as for example phenyllithium or butyllithium.

The compounds of general formula I in which the group $R_1$ is an alkoxyphenyl or haloalkoxyphenyl group etc., and A=CH₂, can also be obtained by treatment of a hydroxyphenyl derivative that can be prepared by hydrolysis of another alkoxyphenyl derivative, for example with the corresponding alkyl halide.

The etherification is generally carried out in solution. Suitable bases include metal alcoholates, such as for example potassium tert.-butylate, metal hydrides, such as for example sodium hydride, metal amides, such as for example lithium diisopropylamide and metal alkyl compounds, such as for example ethyl mangnesium bromide or butyllithium.

Suitable solvents, as opposed to the reactants, especially the bases, include inert substances such as aliphatic and aromatic hydrocarbons such as for example hexane, benzene or toluene and ethers such as for example diethyl ether, tetrahydrofuran or dimethoxyethane. Suitable further amides include dimethylformamide, N-methylpyrrolidone or hexamethylphosphoric acid triamide.

The etherification can further be carried out in a two phase system by using a catalyst and optionally a solvent. Bases that can be used include alkali metal hydroxides or alkali metal carbonates, either as solids or an aqueous solution. Suitable solvents are the reactants themselves as long as they are liquid. Otherwise they can be used in substances which are inert to the bases and which are immiscible with water, such as aliphatic or aromatic hydrocarbons, such as for example hexane, benzene of toluene. Suitable catalysts include crown ethers and quaternary ammonium salts, such are described in Dehmlow and Dehmlow, Phase Transfer Catalysts, Weinheim 1980.

The reaction can be carried out at temperatures between −78° and 140° C., preferably at 20°–80° C., generally at room temperature.

The carbonyl compounds starting materials of general formula IV in which $R_2=H$, and those of general formula VII are known either as such or as their analogues ($R_1$=phenyl) and can be prepared according to methods described in the literature (F. E. Herkes, D. J. Burton, J. Org. Chem. 32, 1316 (1967); R. Stewart, K. C. Teo, Can. J. Chem. 58, 2491 (1980); C. Aaron, D. Dull, J. L. Schmiegel, D. Jaeger, Y. Ohashi, H. S. Mosher J. Org. Chem. 32, 2797 (1967).

The aldehyde compounds of formula IV, used as starting materials, in which $R_2$ is H, can be prepared by reacting a compound of general formula XVIII

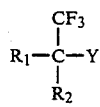
(XVIII)

which can be themselves prepared by methods described in literature, with a cyanisation reagent, such as for example trimethylsilyl cyanide, in the presence of a Lewis acid, such as for example $TiCl_4$ or $SnCl_4$, optionally using a solvent (M. T. Reetz, I. Chatziiosifidis, Angew. Chem. 93. 1075 (1981); R. Davis, K. G. Untch, J. Drg. Chem. 46, 2987 (1981) and then reducing the resulting nitrile of general formula XIX

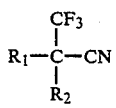
(XIX)

to the desired aldehyde in conventional manner. $R_1$ and $R_2$ have the meanings given above and Y is a hydroxy group or a leaving group, such as for example halogen.

The compounds of general formula XIX, in which the group $R_1$ is an alkoxyphenyl or haloalkoxyphenyl group etc. can be obtained also by treatment of the corresponding hydroxyphenyl derivatives, (which themselves can be prepared by hydrolysis of another alkoxyphenyl derivative), for example by using the corresponding alkyl halide.

The phosphonium salt or phosphonate starting material of general formula II, III and VI can be obtained by treatment of $R_4CH(R_3)CH_2X$ or $R_4CH(R_3)CH_2CH_2X$, wherein X is a halogen atom, with $(R_5)_3P$ or $(R_6O)_3P$.

The alcohols used as starting materials of general formula XIV and XVII can be prepared by reduction of the corresponding nitrile, aldehyde, carboxylic acid or carboxylic acid ester. The reaction can be carried out according to known methods with metal hydride complexes, for example lithium aluminium hydride or alkyl aluminium hydrides for example diisobutylaluminium hydride. The halonide, tosylate and mesylates which are used, are known in themselves or can be prepared according to known methods (DE-OS No. 31 17 510, DE-OS No. 33 17 908, Houben-Wevl, Band 5/4, page 354; ibid. Band 9, page 663).

The compounds of the invention prepared by the above described processes can be isolated from the reaction mixture in conventional manner, for example by distillation of the solvent used at normal or reduced pressure or by extraction.

A higher degree of purity can be obtained as general rule by thin layer chromatography purification or by fractional distillation.

The compounds of the invention are, as a rule, colourless oils that are highly soluble in practically all organic solvents but are almost insoluble in water.

The compounds according to the invention can be used at a concentration of 0.005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may also include phospholipids, e.g. such as from the group phosphatidylcholine, hydrated phosphatidylcholine, phosphatidylethanolamine, N-acyl-phosphatidylethanolamine, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. tonsil, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 3,000 l/ha. The agents can be applies using low-volume or ultra-low-volume techniques or in the form of so-called microgranules.

The preparation of these formulations can be carried out in a known manner, for example by milling or mixing processes. Optionally, individual components can be mixed just before use for example by the so-called commonly used tank-mixing method.

Formulations can be prepared, for example, from the following ingredients.

(a)
80 percent by weight active ingredient
15 percent by weight kaolin 5 percent by weight surface-active agent based on the sodium salt of N-methyl-N-oleyltaurine and the calcium lignosulphonate (b)
45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water (c)
20 percent by weight active ingredient
35 percent by weight bentonite
8 percent by weight calcium lignosulphonate
2 percent by weight of the sodium salt of N-methyl-N-oleyltaurine
35 percent by weight silicic acid (d)
20 percent by weight active ingredient
75 percent by weight isophorone
5 percent by weight of an emulsifier mixture of calcium phenylsulphonate and fatty alcohol polyglycol ether The following examples illustrate the preparation of compounds according to the invention.

EXAMPLE 1

5-(4-Fluoro-3-phenoxyphenyl)-2-(4-methoxyphenyl)-2-trifluoromethylpentane

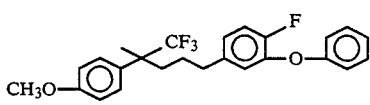

1-(4-Fluoro-3-phenoxyphenyl)-4-(4-methoxyphenyl)-4-trifluoromethyl-2-pentene (15.12 g; 37.76 mmol) was hydrogenated in methanol (200 ml) with hydrogen using Raney nickel (5 g) at room temperature and under atmospheric pressure. After the calculated amount of hydrogen had been taken up, the catalyst was filtered off and the solvent removed under reduced pressure. After chromatography on silica gel using ethyl acetate/hexane as eluant, there was obtained a 10.1 g of product (=61.8% of theory).
$n_D^{20}$:1.5434.

Preparation of the Starting Material

A solution of butyllithium in hexane (1.6 molar; 30 ml) was added, dropwise, under a nitrogen atmosphere to [2-(4-fluoro-3-phenoxyphenyl)ethyl]triphenylphosphonium bromide (26.76 g; 48 mmol) in absolute tetrahydrofuran (200 ml). After stirring for two hours, 2-(4-methoxyphenyl)-2-trifluoromethylpropionaldehyde (10.13 g; 43.63 mmol) dissolve in absolute tetrahydrofuran (80 ml) was added, dropwise. The mixture was heated at reflux for 3 hours and then added to ice-water, extracted with ethyl acetate, the extract dried over sodium sulphate and evaporated. After chromatography on silica gel using hexane/ethyl acetate as eluent, there was obtained 1-(4-fluoro-3-phenoxyphenyl)-4-(4-phenoxyphenyl)-4-trifluoromethyl-2-pentene (15.2 g=80.5% of theory).

A 1.2 molar solution of diisobutylaluminium hydride in toluene (46 ml) was added, dropwise, to 2-(4-methoxyphenyl)-2-trifluoromethylpropionitrile (10.0 g; 43.6 mmol) in absolute toluene (100 ml) at a temperature of 5° to 10° C. After stirring at room temperature for 3 hours, the mixture was added to ice-water, acidified with dilute hydrochloric acid, extracted with ethyl acetate, the organic phase was washed with water and dried over sodium sulphate. There was obtained 2-(4-methoxyphenyl)-2-trifluoromethylpropionaldehyde (9.5 g=93.7% of theory).

Trimethylsilyl cyanide (65.1 ml; 423 mmol) was added at room temperature to 1-chloro-1-(4-methoxyphenyl)-1-trifluoromethylethane (77.6 g; 335.5 mmol) in methylene chloride (975 ml) followed by titanium tetrachloride (32.5 ml; 3.25 mmol). After stirring for 20 hours at room temparature, 2N sodium hydroxide was added carefully, dropwise, until the mixture was neutral and the precipitate separated over celite. The aqueous phase was extracted with ethyl acetate and the extract dried over sodium suphate. After concentrating, there was obtained 2-(4-methoxyphenyl)-2-trifluoromethylpropionitrile (71.49 g=90% of theory).

Titanium tetrachloride (42.3 ml; 42.17 mmol) was added, dropwise, at room temperature to 1-(4-methoxyphenyl)-1-trifluoromethylethanol in methylene chloride (100 ml). After stirring for 1 hour, the mixture was added to ice-water, extracted with methylene chloride, washed first with saturated sodium hydrogen carbonate solution and then with water, dried over sodium sulphate and concentrated. Following distillation in a rotary evaporator at 150° C./0.5 ml, there was obtained 1-chloro-1-(4-methoxyphenyl)-2-trifluoromethylethane (77.67 g=76.7% of theory).

1,1,1-Trifluoroacetone (60.4 ml; 675 mmol) dissolved in absolute ether (80 ml) was added, dropwise, at 5° to 10° C. to an ethereal Grignard solution (prepared from p-bromoanisole (84.17 g; 450 mmol) and magnesium (10.9 g; 450 mmol) in ether (600 ml)) and the mixture stirred at room temperature for 20 hours. It was then added to saturated ammonium chloride solution, extracted with ether and the extract washed with water, dried over sodium sulphate and concentrated. The precipitate was filtered off washed with hexane and the filtrate concentrated. 1-(4-methoxyphenyl)-1-trifluoromethylethanol (93.35 g=94.2% of theory) was obtained as a brown oil that was used without further purification. (The alcohol can also be coverted direct to the nitrile in a one-pot reaction.

EXAMPLE 2

[2-(4-Ethoxyphenyl)-2-trifluoromethylpropyl](4-fluoro-3-phenoxybenzyl)ether

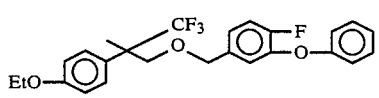

Sodium hydride (144 mg; 6 mmol) was suspended in dimethoxyethane (16 ml) and then in turn, with stirring, there was added 2-(4-ethoxyphenyl)-2-trifluoromethyl-1-propanol (1.25 g; 5.044 mmol), a spatula of sodium iodide and 4-fluoro-3-phenoxybenzyl bromide (1.4 g; 5.04 mmol). After stirring for 5 hours at room temperature, the mixture was added to ice-water, extracted 3 times with ether and the extracts washed with water dried over sodium sulphate and evaporated. After chromatography on silica gel using a mixture of ethyl acetate and hexane, there was obtained 2.06 g of product (=91.1% of theory).
$n^{20}D$; 1.5375.

Preparation of the Starting Material 2-(4-Ethoxyphenyl)-2-trifluoromethylpropionaldehyde (4.23 g; 17.18 mmol), prepared as described in Example 1 for 2-(4-methoxyphenyl)-2-trifluoromethylpropionaldehyde, was reduced with sodium borohydride in isopropanol (Organikum, VEB Deutscher Verlag der Wissenschaften, Berlin 1976, page 616). After working up and chromatography on silica gel using hexane/ethyl acetate, there was obtaine 2.71 g of 2-(4-ethoxyphenyl)-2-trifluoromethyl-1-propanol (=63.7% of theory).

EXAMPLE 3

4-(3-Phenoxyphenyl)-1-phenyl-1-trifluoromethylbutane

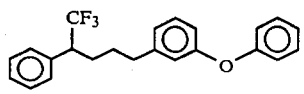

4-(3-Phenoxyphenyl)-1-phenyl-1-trifluoromethyl-1-butene (3.18 g; 8.6 mmol) was hydrogenated in ethanol (40 ml) with hydrogen with the addition of Raney nickel (0.4 g) at room temperature and under atmospheric pressures. After the calculated amount of hydrogen had been taken up, the catalyst was filtered off and the solvent removed under reduced pressure. After chromatography on silica gel with hexane/toluene, there remained 2.49 g of product (=78% of theory).
$n^{20}D$: 1.5463.

Preparation of the Starting Material

A solution of butyllithium in n-hexane (8.5 ml of 1.6 molar) was added, dropwise, at room temperature and under a nitrogen atmosphere over 10 minutes to [3-(3-phenoxyphenyl)propyl]-triphenylphophonium bromide (7.67 g; 13.75 mmol) in absolute tetrahydrofuran (40 ml). After stirring for 2 hours, α,α,α-trifluoroacetophenone (2.18 g; 12.5 mmol) dissolved in absolute tetrahydrofuran (10 ml) was added dropwise. After stirring for 3 hours at room temperature, the mixture was added to ice-water, extracted with ether and the extract dried over sodium sulphate and evaporated. After chromotography on silica gel using hexane-toluene, there was obtained 4-(3-phenoxyphenyl)-1-phenyl-1-trifluoromethyl-1-butene (3.31 g=71.9% of theory).

EXAMPLE 4

3-Phenoxybenzyl 2-phenyl-2-trifluoromethylethyl ether

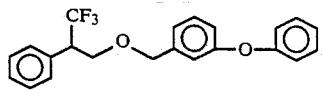

Sodium hydride (138 mg; 5.75 mmol) was suspended in dimethoxyethane (20 ml). There was then added in turn, with stirring, 2-phenyl-2-trifluoromethylethanol (1.0 g; 5.25 mmol), a spatula full of sodium iodide and 3-phenoxybenzyl bromide (1.39 g; 5.25 mmol). After stirring for 4 hours at room temperature, the mixture was added to ice-water, extracted with ether, the extract washed with water, dried over sodium sulphate and concentrated. After chromatogrpahy on silica gel using a mixture of hexane and toluene, there was obtained 1.14 g of product (=58.3% of theory).
$n^{20}D$: 1,546.

Preparation of the Starting Material

A 20% solution of diisobutylaluminium hydride in n-hexane (53.4 ml) was added, dropwise, to ethyl α-trifluoromethylphenylacetate (2.9 g; 12.5 mmol) (T. S. Everett, S. T. Purrington, C. L. Baumgardner, J. Org. Chem. 49, 3702 (1984)) in absolute tetrahydrofuran (50 ml) at about 60° C. The mixture was then allowed to rise to room temperature and stirred for an hour at this temperature. Then at a temperature of 5°–10° C., methanol (10.5 ml) followed by 10% aqueous potassium hydroxide (5.3 ml) was added, dropwise. After 1.5 hours, the mixture was filtered and the filtrate dried over sodium sulphate which was washed with ethyl acetate and the organic phase concentrated. There was obtained 2-phenyl-2-trifluoromethylethanol (2.07 g=87.1 of theory).

In a similar way the following compounds were prepared:

| Example No. | Compound | Physical constant $n_D^{20}$ |
|---|---|---|
| 5 | 2-(4-Ethoxyphenyl)-2-trifluoromethylpropyl 3-phenoxybenzyl ether | 1.5451 |
| 6 | 2-(4-Ethoxyphenyl)-2-trifluoromethylpropyl 3-(N—methylanilino)benzyl ether | 1.5542 |
| 7 | 2-(4-Methoxyphenyl)-2-trifluoromethylpropyl 3-phenoxybenzyl ether | 1.5498 |
| 8 | 2,6-Dichlorobenzyl 2-(4-methoxyphenyl)-2-trifluoromethylpropyl ether | 1.5358 |
| 9 | 4-Fluoro-3-phenoxybenzyl 2-(4-methoxyphenyl)-2-trifluoromethylpropyl ether | 1.5402 |
| 10 | 2-(4-Difluoromethoxyphenyl)-2-trifluoromethylpropyl 3-phenoxybenzyl ether | 1.5239 |
| 11 | 2-(4-Isopropoxyphenyl)-2-trifluoromethylpropyl 3-phenoxybenzyl ether | 1.5418 |
| 12 | 4-Fluoro-3-phenoxybenzyl 2-(4-isopropoxyphenyl)-2-trifluoromethylpropyl ether | 1.5331 |
| 13 | 2-(4-Isopropoxyphenyl)-2-trifluoromethylpropyl 6-phenoxy-2-pyridylmethyl ether | 1.5390 |
| 14 | 2-(4-Butoxyphenyl)-2-trifluoromethylpropyl 3-phenoxybenzyl ether | 1.5380 |
| 15 | 2-(4-Butoxyphenyl)-2-trifluoromethylpropyl 4-fluoro-3-phenoxybenzyl ether | 1.5305 |
| 16 | 2-[4-(2-fluoroethoxy)phenyl]-2-trifluoromethylpropyl 3-phenoxybenzyl ether | 1.5422 |
| 17 | 4-Fluoro-3-phenoxybenzyl 2-[4-(2-fluoroethoxy)phenyl]-2-trifluoromethylpropyl ether | 1.5350 |
| 18 | 2-(4-Ethoxyphenyl)-2-trifluoromethylpropyl 6-phenoxy-2-pyridylmethyl ether | 1.5440 |
| 19 | 2-(4-Difluoromethoxyphenyl)-2-trifluoromethylpropyl 4-fluoro-3-phenoxybenzyl ether | 1.5203 |
| 20 | 2-(4-Butoxyphenyl)-2-trifluoromethylpropyl 3-(N—methylanilino)benzyl ether | 1.5542 |
| 21 | 2-(4-Difluoromethoxyphenyl)-2-trifluoromethylpropyl 6-phenoxy-2-pyridylmethyl ether | 1.5256 |
| 22 | 2-(4-Ethoxyphenyl)-5-(4-fluoro-3-phenoxyphenyl)-2-trifluoromethylpentane | 1.5392 |
| 23 | 5-(4-Fluoro-3-phenoxyphenyl)-2-(4-isopropoxyphenyl)-2-trifluoromethylpentane | 1.5350 |
| 24 | 2-(4-Difluoromethoxyphenyl)-5-(4-fluoro-3-phenoxyphenyl)-2-trifluoromethylpentane | 1.5223 |
| 25 | 2-(4-Methoxyphenyl)-5-(3-phenoxyphenyl)-2-trifluoromethylpentane | 1.5505 |
| 26 | 5-(3-Phenoxyphenyl)-2-trifluoromethyl-2-(4-trifluoromethylsulphonyloxyphenyl)pentane | 1.5130 |
| 27 | 2-(4-Ethoxyphenyl)-5-(3-phenoxyphenyl)-2-trifluoromethylpentane | 1.5454 |
| 28 | 2-(4-Isopropoxyphenyl)-5-(3-phenoxyphenyl)-2-trifluoromethylpentane | 1.5410 |
| 29 | 2-(4-Difluoromethoxyphenyl)-5-(3-phenoxyphenyl)-2-trifluoromethylpentane | 1.5280 |
| 30 | 2-[4-(2,2-Dichlorovinyloxy)phenyl]-5- | 1.5596 |

-continued

| Example No. | Compound | Physical constant $n_D^{20}$ |
|---|---|---|
|  | (3-phenoxyphenyl)-2-trifluoromethylpentane |  |
| 31 | 4-Fluoro-3-phenoxybenzyl 2-phenyl]-2-trifluoromethylethyl ether | 1.5380 |
| 32 | 1-(4-Methoxyphenyl)-4-(3-phenoxyphenyl)-1-trifluoromethylbutane | 1.5461 |
| 33 | 1-(4-Ethoxyphenyl)-4-(3-phenoxyphenyl)-1-trifluoromethylbutane | 1.5440 |
| 34 | 1-(4-Isopropoxyphenyl)-4-(3-phenoxyphenyl)-1-trifluoromethylbutane | 1.5391 |
| 35 | 1-(4-Difluoromethoxyphenyl)-4-(3-phenoxyphenyl)-1-trifluoromethylbutane | 1.5264 |
| 36 | 4-(3-Phenoxyphenyl)-1-trifluoromethyl-1-(4-trifluoromethylsulphonyloxyphenyl)butane | 1.5122 |
| 37 | 1-(Fluorophenyl)-4-(3-phenoxyphenyl)-1-trifluoromethylbutane | 1.5360 |
| 38 | 1-(Methylphenyl)-4-(3-phenoxyphenyl)-1-trifluoromethylbutane | 1.5430 |
| 39 | 4-(4-Fluoro-3-phenoxyphenyl)-1-(4-methoxyphenyl)-1-trifluoromethylbutane | 1.5393 |
| 40 | 1-(4-Ethoxyphenyl)-4-(4-fluoro-3-phenoxyphenyl)-1-trifluoromethylbutane | 1.5350 |
| 41 | 4-(4-Fluoro-3-phenoxyphenyl)-1-(4-isopropoxyphenyl)-1-trifluoromethylbutane | 1.5303 |
| 42 | 4-(4-Fluoro-3-phenoxyphenyl)-1-trifluoromethyl-1-(4-trifluoromethylsulphonyloxyphenyl)butane | 1.5048 |
| 43 | 1-(4-Difluoromethoxyphenyl)-4-(4-fluoro-3-phenoxyphenyl)-1-trifluoromethylbutane | 1.5178 |
| 44 | 4-(4-Fluoro-3-phenoxyphenyl)-1-(4-methylphenyl)-1-trifluoromethylbutane | 1.5356 |
| 45 | 4-(4-Fluoro-3-phenoxyphenyl)-1-(4-fluorophenyl)-1-trifluoromethylbutane | 1.5278 |
| 46 | 4-(4-Fluoro-3-phenoxyphenyl)-1-(3,4-methylenedioxyphenyl)-1-trifluoromethylbutane | 1.5460 |
| 47 | 2-(4-Fluoro-3-phenoxyphenyl)-2-(trifluoromethylpropyl) 3-phenoxybenzyl ether | 1.5385 |
| 48 | 2-(4-Fluoro-3-phenoxyphenyl)-2-(trifluoromethylpropyl) 4-fluoro-3-phenoxybenzyl ether | 1.5350 |
| 49 | 2-(Ethoxy-3-fluorophenyl)-2-(trifluoromethylpropyl) 3-phenoxybenzyl ether | 1.5376 |
| 50 | 2-(4-Ethoxy-3-fluorophenyl)-2-(trifluoromethylpropyl) 4-fluoro-3-phenoxybenzyl ether | 1.5312 |
| 51 | 2-(Methoxyphenyl)-2-(trifluoromethylethyl) 3-phenoxybenzyl ether | 1.5490 |
| 52 | 4-Fluoro-3-phenoxybenzyl 2-(4-methoxyphenyl)-2-trifluoromethylethyl ether | 1.5400 |
| 53 | 2-(4-Methoxyphenyl)-2-(trifluoromethylethyl) 6-phenoxy-2-pyridylmethyl ether | 1.5422 |
| 54 | 4-(4-Fluoro-3-phenoxyphenyl)-1-[4-(2-fluoroethoxy)phenyl]-1-trifluoromethylbutane | 1.5319 |
| 55 | 1-[4-(2,2-Difluorocyclopropylmethoxy)phenyl]-4-(4-fluoro-3-phenoxyphenyl)-1-trifluoromethylbutane | 1.5244 |
| 56 | 4-(4-Fluoro-3-phenoxyphenyl)-1-[4-(2,2,3,3-tetrafluoropropoxy)phenyl]-1-trifluoromethylbutane | 1.5060 |
| 57 | 1-[4-(2,2-Dichlorocyclopropylmethoxy)phenyl]-4-(4-fluoro-3-phenoxyphenyl)-1-trifluoromethylbutane | 1.5450 |
| 58 | 1-(4-Ethenyloxyphenyl)-4-(4-fluoro-3-phenoxyphenyl)-1-trifluoromethylbutane | 1.5408 |
| 59 | 4-(4-Fluoro-3-phenoxyphenyl)-1-[4-(2,2,2-trifluoroethoxy)phenyl]-1-trifluoromethylbutane | 1.5101 |
| 60 | 1-[4-(2,2-Difluorocyclopropyloxy)phenyl]-4-(4-fluoro-3-phenoxyphenyl)-1-trifluoromethylbutane | 1.5240 |
| 61 | 1-[4-(2,2,2-Trichloro-1,1-difluoroethoxy)phenyl]-4-(4-fluoro-3-phenoxyphenyl)-1-trifluoromethylbutane | 1.5236 |
| 62 | 1-(3-Fluoro-4-methoxyphenyl)-4-(3-phenoxyphenyl)-1-trifluoromethylbutane | 1.5420 |
| 63 | 1-(4-tert.-Butylphenyl)-4-(3-phenoxyphenyl)-1-trifluoromethylbutane | 1.5366 |
| 64 | 2-(4-Ethoxyphenyl)-2-(trifluoromethylethyl) 3-phenoxybenzyl ether | 1.5444 |
| 65 | 1-(4-Ethoxy-3-fluorophenyl)-4-(3-phenoxyphenyl)-1-trifluoromethylbutane | 1.5376 |
| 66 | 2-(4-Ethoxyphenyl)-2-(trifluoromethylethyl) 4-fluoro-3-phenoxy-benzyl ether | 1.5358 |
| 67 | 4-(4-Fluoro-3-phenoxyphenyl)-1-(3-fluorophenyl)-1-trifluoromethylbutane | 1.5286 |
| 68 | 1-(3-Fluorophenyl)-4-(3-phenoxyphenyl)-1-trifluoromethylbutane | 1.5360 |
| 69 | 4-(4-Fluoro-3-phenoxyphenyl)-1-(3,4-difluorophenyl)-1-trifluoromethylbutane | 1.5210 |
| 70 | 1-(3,4-Difluorophenyl)-4-(3-phenoxyphenyl)-1-trifluoromethylbutane | 1.5290 |
| 71 | 1-(4-tert.-Butylphenyl)-4-(4-fluoro-3-phenoxyphenyl)-1-trifluoromethylbutane | 1.5280 |
| 72 | 1-(3-Fluoro-4-methoxyphenyl)-4-(4-fluoro-3-phenoxyphenyl)-1-trifluoromethylbutane | 1.5330 |
| 73 | 1-(4-Ethoxy-3-fluorophenyl)-4-(4-fluoro-3-phenoxyphenyl)-1-trifluoromethylbutane | 1.5294 |
| 74 | 1-(4-Difluoromethoxy-3-fluorophenyl]-4-(4-fluoro-3-phenoxyphenyl)-1-trifluoromethylbutane | 1.5119 |
| 75 | 1-(3-Fluoro-4-isopropoxyphenyl)-4-(4-fluoro-3-phenoxyphenyl)-1-trifluoromethylbutane | 1.5215 |
| 76 | 4-(3-Phenoxyphenyl)-1-(5,6,7,8-tetrahydro-2-naphthyl)-1-trifluoromethylbutane | 1.5534 |
| 77 | 1-(5-Indanyl)-4-(3-phenoxyphenyl)-1-trifluoromethylbutane | 1.5541 |
| 78 | 1-(4-Phenoxyphenyl)-4-(3-phenoxyphenyl)-1-trifluoromethylbutane | 1.5694 |
| 79 | 4-(4-Fluoro-3-phenoxyphenyl)-1-(5-Indanyl)-1-trifluoromethylbutane | 1.5461 |
| 80 | 4-(4-Fluoro-3-phenoxyphenyl)-1-(5,6,7,8-tetrahydro-2-naphthyl)-1-trifluoromethylbutane | 1.5380 |
| 81 | 1-(4-Fluorophenyl)-4-[3-(4-methoxyphenoxy)phenyl]-1-trifluoromethylbutane | 1.5380 |
| 82 | 4-(4-Fluoro-3-phenoxyphenyl)-1-(4-phenoxyphenyl)-1-trifluoromethylbutane | 1.5585 |
| 83 | 1-(4-Fluorophenyl)-(4-pentafluorophenyl)-1-trifluoromethylbutane | 1.4587 |
| 84 | 4-[3-(4-Chlorophenoxy)phenyl]-1-(4-fluorophenyl)-1-trifluoromethylbutane | 1.5405 |
| 85 | 4-[3-tert.-Butylphenoxy)phenyl]-1-(4-fluorophenyl)-1-trifluoromethylbutane | 1.5272 |
| 86 | 1-(4-Fluorophenyl)-1-trifluoromethyl-4-[3-(3-trifluoromethylphenoxy)phenyl]butane | 1.5037 |
| 87 | 1-(4-Fluorophenyl)-4-[3-(4-methylphenoxy)phenyl]-1-trifluoromethylbutane | 1.5340 |
| 88 | 4-(4-Dimethylaminophenyl)-1-(4-fluorophenyl)-1-trifluoromethylbutane | 1.5221 |
| 89 | 4-[4-(1,1,2,2-tetrafluoroethoxy)phenyl]-1-(4-fluorophenyl)-1-trifluoromethylbutane | 1.4580 |
| 90 | 1-(4-Fluorophenyl)-4-(6-phenoxy-2-pyridyl)-1-trifluoromethylbutane | 1.5316 |
| 91 | 4-(3-Anilinophenyl)-1-(4-fluorophenyl)-1-trifluoromethylbutane | 1.5620 |
| 92 | 1-(4-Fluorophenyl)-4-(2,6-difluoro-2-phenyl)-1-trifluoromethylbutane | 1.4780 |
| 93 | 4-(2-Fluorenyl)-1-(4-fluorophenyl)-1-trifluoromethylbutane | 1.5648 |
| 94 | 1-(4-Ethoxyphenyl)-1-trifluoromethyl-4-[3-(3-trifluoromethylphenoxyphenyl]butane | 1.5144 |
| 95 | 1-(4-Ethoxyphenyl)-4-[3-(4-methoxyphenoxy)phenyl]-1-trifluoromethylbutane | 1.5436 |
| 96 | 4-(3-Anilino-4-phenyl)-1-(4-fluorophenyl)-1-trifluoromethylbutane | 1.5550 |
| 97 | 1-(4-Fluorophenyl)-4-(3,4-methylenedioxyphenyl)-1-trifluoromethylbutane | 1.5120 |
| 98 | 1-(4-Ethoxyphenyl)-4-(6-phenoxy-2-pyridyl)-1-trifluoromethylbutane | 1.5405 |
| 99 | 4-[3-(4-tert.-Butylphenoxy)phenyl]-1-(4-ethoxyphenyl)-1-trifluoromethylbutane | 1.5356 |
| 100 | 4-(3-Phenoxyphenyl)-1-trifluoromethyl-1-(3-trifluoromethylphenyl)butane | 1.5149 |
| 101 | 4-(4-Fluoro-3-phenoxy)phenyl]-1-trifluoromethyl-1-(3-trifluoromethylphenyl)butane | 1.5078 |
| 102 | 1-(4-Fluorophenyl)-4-(2,3-methylenedioxyphenyl)-1-trifluoromethylbutane | 1.5094 |
| 103 | 4-(4-Ethoxy-2,3,4,5-tetrafluorophenyl-1-(4-fluorophenyl)-1-trifluoromethylbutane | 1.4669 |
| 104 | 1-(4-Allyloxyphenyl)-4-(3-phenoxyphenyl)-1-trifluoromethylbutane | 1.5465 |
| 105 | 1-(4-Allyloxyphenyl)-4-(4-fluoro-3-phenoxy- | 1.5391 |

-continued

| Example No. | Compound | Physical constant $n_D^{20}$ |
|---|---|---|
| | phenyl)-1-trifluoromethylbutane | |
| 106 | 4-(3-Phenoxyphenyl)-1-(4-propargyloxy-phenyl)-1-trifluoromethylbutane | 1.5502 |
| 107 | 4-(4-Fluoro-3-phenoxyphenyl)-1-(4-propargyloxyphenyl)-1-trifluoromethylbutane | 1.5430 |
| 108 | 1-[4-(But-2-inyloxy)phenyl]-4-(3-phenoxyphenyl)-1-trifluoromethylbutane | 1.5510 |
| 109 | 1-[ 4-(But-2-inyloxy)phenyl]-4-(fluoro-3-phenoxyphenyl)-1-trifluoromethylbutane | 1.5510 |
| 110 | 1-(4-Bromophenyl)-4-(3-phenoxyphenyl)-1-trifluoromethylbutane | |
| 111 | 1-(4-Chlorophenyl)-4-(3-phenoxyphenyl)-1-trifluoromethylbutane | |
| 112 | 1-(4-Bromophenyl)-4-(4-fluoro-3-phenoxyphenyl)-1-trifluoromethylbutane | |
| 113 | 1-(4-Chlorophenyl)-4-(3-phenoxyphenyl)-1-trifluoromethylbutane | |
| 114 | 1,4-Bis-(4-Fluorophenyl)-1-trifluoromethylbutane | 1.4860 |
| 115 | 1-(4-Fluorophenyl)-4-(3-methoxyphenyl)-1-trifluoromethylbutane | 1.5040 |
| 116 | 1-(4-Fluorophenyl)-1-trifluoromethyl-4-(3-trifluoromethylphenyl)butane | 1.4660 |
| 117 | 4-[3-(3,4-Dichlorophenoxy)phenyl]-1-(4-Fluorophenyl)-1-trifluoromethylbutane | 1.5493 |
| 118 | 2-(4-Ethoxyphenyl)-2-(trifluoromethyl-ethyl 4-(2-fluoroethoxy)benzyl ether | |
| 119 | 2-(4-Ethoxyphenyl)-2-(trifluoromethyl-ethyl 3-(2-fluoroethoxy)benzyl ether | |
| 120 | 2-(4-Chlorophenyl)-2-(trifluoromethyl-ethyl 4-(2-fluoroethoxy)benzyl ether | |
| 121 | 2-(4-Chlorophenyl)-2-(trifluoromethyl-ethyl 3-(2-fluoroethoxy)benzyl ether | |
| 122 | 1-(4-Fluorophenyl)-4-[3-(2-fluoroethoxy)-phenyl]-1-trifluoromethylbutane | |
| 123 | 1-(4-Fluorophenyl)-4-[4-(2-fluoroethoxy)-phenyl]-1-trifluoromethylbutane | |
| 124 | 1-(4-Ethoxyphenyl)-4-[4-(2-fluoroethoxy)phenyl]-1-trifluoromethylbutane | |
| 125 | 1-(4-Ethoxyphenyl)-4-[3-(2-fluoroethoxy)-phenyl]-1-trifluoromethylbutane | |
| 126 | 1-(4-Chlorophenyl)-4-[3-(2-fluoroethoxy)-phenyl]-1-trifluoromethylbutane | |
| 127 | 1-(4-Chlorophenyl)-4-[4-(2-fluoroethoxy)-phenyl]-1-trifluoromethylbutane | |

The following test Examples illustrate the possible uses of the compounds of the invention that have been suitably formulated for use.

TEST EXAMPLE 1

Activity against Wingless Stages of Black Bean Aphids (*Aphis fabae*)

Compounds of the invention were made up as aqueous emulsions at a concentration of 0.1%. Broad bean (*Vicia fabae*) plants (one plant per pot) that had previously been infested with wingless stages of the black bean aphid (*Aphis fabae*) were sprayed until dripping wet with these preparations. After this, the treated test samples were left in the laboratory under extended daylight conditions for 48 hours. The % mortality of the larvae after 48 hours from the start of the experiment in comparison with untreated controls indicated the level of activity.

In this experiment, the compounds of the preparative Examples 1–43, 44–46, 48–51, 53, 64, 66, 67, 69–75, 77, 79, 98 and 101 showed 100% activity.

TEST EXAMPLE 2

Activity against Larvae of the Diamond-Backed Moth (*Plutella xylostella*).

The compounds of the invention were made up as aqueous emulsions at a concentration of 0.1%. Cabbage leaves (*Brassica olearacea* var. *botrytis*), placed in polystyrene petri dishes, were sprayed with these preparations (4 mg spray/cm$^2$). After the sprayed surface had dried, 10 young larvae of the diamond-backed moth (*Plutella xylostella*) were placed in each petri dish and thereby exposed to the treated food in the closed dishes for two days. The % mortality of the larvae after two days indicated the level of activity.

In this experiment, the compounds of the preparative Examples 2, 3, 4, 9, 19, 22, 24, 31–54, 56, 58–60, 62, 72–75, 79–82, 84, 87, 90, 93, 95–98, 100 and 101 showed 100% activity.

TEST EXAMPLE 3

Activity against Larvae (L3) of the Mexican Bean Beetle (*Epilachna varivestis*)

The compounds of the invention were made up as aqueous emulsions at a concentration of 0.1%. French bean plants (*Phaseolus vulgaris*) in the primary leaf stage were dipped in the preparations. For each test, two plant stems with in total four primary leaves were placed in glass vases filled with water and enclosed in plexiglass cylinders. Then five larvae of the Mexican bean beetle (*Epilachna varivestis*) at the third larval stage were put in the glass cylinders and kept for three days under extended daylight conditions. The % mortality of the larvae after three days indicated the level of activity.

In these experiments the compounds of Examples 2, 4, 5, 9, 11, 22, 24, 28, 33 and 62–66 showed 100% mortality.

TEST EXAMPLE 4

Activity against Larvae (L2) of the Cotton Army Worm (*Spodoptera littoralis*)

Compounds of the invention were made up as aqueous emulsions at a concentration of 0.1%. Leaflet pairs of beans (*Vicia fabae*) as well as 10 larvae (L2) of the cotton army worm (*Spodoptera littoralis*) per experiment were sprayed with 4 mg spray/cm$^2$ of these preparations in polystyrene petri dishes. The closed petri dishes were left in the laboratory under extended daylight conditions for two days. The % mortality of the larvae after two days indicated the level of activity.

In this experiment, the compounds of the preparative Examples 2, 3, 4, 9, 12, 17, 18, 21, 33–46, 49, 50, 52, 54, 58–60, 62, 64–70, 72, 75, 84, 90, 96, 98, 100 and 101 showed 100% activity.

TEST EXAMPLE 5

Ovicidal Activity against Eggs of the Cotton Army Worm (*Spodoptera littoralis*)

The compounds of the invention were made up as aqueous emulsions at a concentration of 0.1%. One day old eggs that had been laid on filter paper by fertilised female moths were dipped in the preparations until they were completely wet and then placed in closed petri dishes in the laboratory under extended daylight conditions for four days. The % inhibition of hatching of the eggs in comparison with untreated eggs indicates the level of activity.

In this experiment, the compounds of the preparative Examples 2, 4, 5, 64–66, 72, 73, 77, 87, 90 and 96 showed 100% activity.

TEST EXAMPLE 6

Activity against Motile Stages and Eggs of the Two Spotted Spider Mite (*Tetranychus urticae*)

Compounds of the invention were made up as an aqueous emulsion at a concentration of 0.1%. Dwarf bean plants (*Phaseolus vulgaris*) in the primary leaf stage, which had been infested with spider mites (*Tetranychus urticae*), were sprayed with these preparations until they were dripping wet and left in a laboratory for seven days under extende daylight conditions. After this, the % mortality of the motile stages on the one hand and the eggs on the other hand were estimated in comparison with untreated controls, using a magnifying glass.

In this experiment, the compounds of the preparative Examples 11, 12, 13, 19, 23, 24, 66, 69, 74, 75, 82, 84, 87 and 90–96 showed 100% activity.

TEST EXAMPLE 7

Activity in Prophylactic Treatment of Leaves against Brown Rice-Hoppers (*Niliparvata lugens Stal*)

In a heated greenhouse, rice seedlings (about 15 per pot) were grown until formation of the third leaf and then sprayed until dripping wet with an aqueous preparation containing 0.1% of active material. After drying the sprayed leaves, a transparent cylinder was placed over each pot. 30 Adult brown rice-hoppers (*Niliparvata lugens*) were introduced into each pot. After 2 days at 26° C. in the greenhouse, the amount of dead hoppers was determined. The activity was calculated according to Abbott in comparison with several untreated control pots.

Complete death was reached with the compounds of Examples 4, 12, 19, 22, 24, 33, 35–46, 49–55, 59–62, 64–81, 83, 84, 90, 94–96 and 114.

TEST EXAMPLE 8

Tickicidal Activity against *Boophilus microplus*

9 cm diameter filter papers were impregnated with 1 ml aliquots of acetone solutions of test compound at various concentrations. The papers were allowed to dry and then folded into envelopes in which cattle tick larvae, (*Boophilus micoplus*) were enclosed and held at 25° C. and 80% R.H. for 48 hours. The percentage mortality of tick larvae was then recorded and compared with controls.

The controls gave a mortality of less than 5% whereas compounds of Examples 2, 3, 5, 9, 10, 11, 12, 13, 22, 25, 26, 28, 32, 33, 37–46, 48, 51–55, 57, 58, 60, 62–67, 69–72, 74, 76, 77 and 79–81. caused 50% mortality at a concentration of 300 ppm or less.

TEST EXAMPLE 9

Insecticidal Activity against *Lucilia sericata*

1 ml aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blowfly (*Lucilia sericata*), closed by a cotton wool plug and held at 25° C. for 24 hours.

For the controls the morality was <5% whereas the compounds of Examples 2, 5, 7, 9–18, 22, 23, 28, 32–35, 37–46, 51–55, 57, 58, 60–67, 69–72, 74, 76, 77 and 79–81 had an $LC_{50}$ of 100 ppm or less.

TEST EXAMPLE 10

Insecticidal Activity against *Musca domestica*

Aliquots of acetone solutions of test compounds at various concentrations were applied to 9 cm diameter filter papers placed in the bottom of 9 cm diameter petri dishes closed by glass lids. After evaporation of solvent, the treated surfaces, together with control treated with acetone alone, were then infested with adult houseflies, (*Musca domestica*) and held at 22° C. for 24 hours.

The percentage mortality of the insects was then recorded. Less than 5% mortality resulted in the control treatments whereas the compounds of Examples 2, 5, 9, 10, 11, 12, 18, 32, 39, 40, 43, 44 and 66 had an $LC_{50}$ of 400 mg/m² or less.

TEST EXAMPLE 11

Insecticidal Activity against *Blattella germanica*

Aliquots of acetone solutions of test compounds at various concentrations were applied to glass plates (10 cm×10 cm). After evaporation of solvent, the treated surfaces, together with controls treated with acetone alone, were then infested with second instar nymphs of the German cockroach, (*Blattella germanica*), retained on the treated surface within PTFE-coated glass rings 6 cm in diameter and held for 24 hours at 22° C. The percentage mortality of the insects was then recorded.

Less than 5% mortality resulted in the control treatments whereas the compounds of Examples 2, 3, 5, 7, 9, 11–13, 16, 17, 22, 23, 25, 27, 29, 32, 33, 37–46, 51–55, 57, 58, 60–62, 67, 69–72, 74, 76, 77 and 79–81 had an $LD_{50}$ of 100 mg/m² or less.

We claim:

1. An alkane or alkoxyalkane derivative of the formula

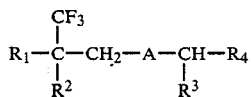

in which
R$_1$ is aryl or heteroaryl or these groups substituted by C$_{1-4}$ alkyl, halo-C$_{1-4}$ alkyl, phenyl-C$_{1-4}$ alkyl, C$_{2-4}$ alkenyl, halo-C$_{2-4}$ alkenyl, phenyl-C$_{2-4}$ alkenyl, C$_{2-4}$ alkynyl, halo-C$_{2-4}$ alkynyl, phenyl-C$_{2-4}$ alkynyl, C$_{1-4}$ alkoxy, halo-C$_{1-4}$ alkoxy, phenyl-C$_{1-4}$ alkoxy, C$_{2-4}$ alkenyloxy, halo-C$_{2-4}$ alkenyloxy, phenyl-C$_{2-4}$ alkenyloxy, C$_{2-4}$ alkynyloxy, halo-C$_{2-4}$ akynyloxy, phenyl-C$_{2-4}$ alkynyloxy, alkylsulphonyloxy, haloalkylsulphonyloxy, arylsulphonyloxy, halo, cyano, nitro, aryloxy, haloaryloxy, C$_{1-4}$ alkylaryloxy, or nitroaryloxy, wherein heteroaryl is benzofuranyl, benzothiophenyl, benzoxazolyl, indanyl or benzodioxanyl
R$_2$ is hydrogen or C$_{1-4}$ alkyl,
R$_3$ is hydrogen, cyano or ethynyl,
R$_4$ is phenyl or pyridyl or these groups substituted by at least one of C$_{1-6}$ alkyl, halo-C$_{1-6}$ alkyl, phenyl-C$_{1-6}$ alkyl, C$_{2-6}$ alkyl interrupted by an O-, N- or S-atom, C$_{2-4}$ alkenyl, halo-C$_{2-4}$ alkenyl, phenyl-C$_{2-}$ 4 alkenyl, $C_{1-4}$ alkoxy, halo-$C_{1-4}$ alkoxy, phenyl-$C_{1-4}$ alkoxy, $C_{2-4}$ alkenyloxy, halo-$C_{2-4}$ alkenyloxy, phenyl-$C_{2-4}$ alkenyloxy, $C_{2-4}$ alkynyloxy, halo-$C_{2-4}$ alkynyloxy, phenyl-$C_{2-4}$ alkynyloxy, aryloxy, haloaryloxy, $C_{1-4}$ alkylaryloxy, arylamino, haloarylamino, $C_{1-4}$ alkylarylamino, aryl-N-$C_{1-4}$ alkylamino, aryl-N-$C_{1-4}$ acylamino, aroyl, haloaroyl, $C_{1-4}$ alkylaroyl, aryl, haloaryl, $C_{1-4}$ alkylaryl or halo, and A is $CH_2$ or O.

2. Alkane or alkoxyalkane derivative according to claim 1, in which $R_1$ is chlorophenyl, bromophenyl, fluorophenyl, methylphenyl, methoxyphenyl, ethoxyphenyl, difluoromethoxyphenyl, fluoroethoxyphenyl, or trifluoroethoxyphenyl, $R_2$ is hydrogen or methyl, $R_3$ is hydrogen, $R_4$ is phenoxyphenyl, fluorophenoxyphenyl or phenoxypyridyl and A is $CH_2$ or O.

3. Insecticidal and acaricidal composition which comprises a compound claimed in claim 1 in admixture with an agriculturally acceptable diluent.

4. A method of combating insects and acarids which comprises applying to the insects or acarids or their locus an effective amount of a compound claimed in claim 1.

5. The method of claim 4 in which said compound is [2-(4-ethoxyphenyl)-2-trifluoromethylpropyl](4-fluoro-3-phenoxybenzyl)ether, 2-phenoxybenzyl 2-phenyl-2-trifluoromethylethyl ether or 4-fluoro-3-phenoxybenzyl 2-(4-methoxyphenyl)-2-trifluoromethylpropyl ether.

6. The method of claim 4 in which said compound is 5-(4-fluoro-3-phenoxyphenyl)-2-(4-methoxyphenyl)-2-trifluoromethylpentane, 4-(3-phenoxyphenyl)-1-phenyl-1-trifluoromethylbutane, 1-(4-ethoxyphenyl)-4-(3-phenoxyphenyl)-1-trifluoromethylbutane, 1-(3-fluoro-4-methoxyphenyl)-4-(4-fluoro-3-phenoxyphenyl)-1-trifluoromethylbutane, 1-(3-fluoro-4-isopropoxyphenyl)-4-(4-fluoro-3-phenoxyphenyl)-1-trifluoromethylbutane, 1-(4-ethoxyphenyl)-4-(6-phenoxy-2-pyridyl)-1-trifluoromethylbutane, 4-(3-phenoxyphenyl)-1-trifluoromethyl-1-(3-trifluoromethylphenyl)butane, or [4-(4-fluoro-3-phenoxy)phenyl]-1-trifluoromethyl-1-(3-trifluoromethylphenyl)butane.

7. A method of combatting insects and acarids which comprises applying to the insects or acarids or to their locus an effective amount of a compound claimed in claim 2.

8. Insecticidal and acaricidal composition according to claim 3 in which said compound is [2-(4-ethoxyphenyl)-2-trifluoromethylpropyl](4-fluoro-3-phenoxybenzyl)ether, 2-phenoxybenzyl 2-phenyl-2-trifluoromethylethyl ether or 4-fluoro-3-phenoxybenzyl 2-(4-methoxyphenyl)-2-trifluoromethylpropyl ether.

9. Insecticidal and acaricidal composition according to claim 3 in which said compound is 5-(4-fluoro-3-phenoxyphenyl)-2-(4-methoxyphenyl)-2-trifluoromethylpentane, 4-(3-phenoxyphenyl)-1-phenyl-1-trifluoromethylbutane, 1-(4-ethoxyphenyl)-4-(3-phenoxyphenyl)-1-trifluoromethylbutane, 1-(3-fluoro-4-methoxyphenyl)-4-(4-fluoro-3-phenoxyphenyl)-1-trifluoromethylbutane, 1-(3-fluoro-4-isopropoxyphenyl)-4-(4-fluoro-3-phenoxyphenyl)-1-trifluoromethylbutane, 1-(4-ethoxyphenyl)-4-(6-phenoxy-2-pyridyl)-1-trifluoromethylbutane, 4-(3-phenoxyphenyl)-1-trifluoromethyl-1-(3-trifluoromethylphenyl)butane, or [4-(4-fluoro-3-phenoxy)phenyl]-1-trifluoromethyl-1-(3-trifluoromethylphenyl)butane.

10. Insecticidal and acaricidal composition which comprises a compound claimed in claim 2 in admixture with an agriculturally acceptable diluent.

11. Alkane or alkoxyalkane derivative according to claim 1 which is [2-(4-ethoxyphenyl)-2-trifluoromethylpropyl](4-fluoro-3-phenoxybenzyl)ether, 2-phenoxybenzyl 2-phenyl-2-trifluoromethylethyl ether or 4-fluoro-3-phenoxybenzyl 2-(4-methoxyphenyl)-2-trifluoromethylpropyl ether.

12. Alkane or alkoxyalkane derivative according to claim 1 which is 5-(4-fluoro-3-phenoxyphenyl)-2-(4-methoxyphenyl)-2-trifluoromethylpentane, 4-(3-phenoxyphenyl)-1-phenyl-1-trifluoromethylbutane, 1-(4-ethoxyphenyl)-4-(3-phenoxyphenyl)-1-trifluoromethylbutane, 1-(3-fluoro-4-methoxyphenyl)-4-(4-fluoro-3-phenoxyphenyl)-1-trifluoromethylbutane, 1-(3-fluoro-4-isopropoxyphenyl)-4-(4-fluoro-3-phenoxyphenyl)-1-trifluoromethylbutane, 1-(4-ethoxyphenyl)-4-(6-phenoxy-2-pyridyl)-1-trifluoromethylbutane, 4-(3-phenoxyphenyl)-1-trifluoromethyl-1-(3-trifluoromethylphenyl)butane, and [4-(4-fluoro-3-phenoxy)phenyl]-1-trifluoromethyl-1-(3-trifluoromethylphenyl)butane.

* * * * *